United States Patent [19]

Cornelius

[11] Patent Number: 5,649,909
[45] Date of Patent: Jul. 22, 1997

[54] VARIABLE STIFFNESS MULTI-LUMEN CATHETER

[75] Inventor: Richard George Cornelius, Golden Valley, Minn.

[73] Assignee: SciMed Life Systems, Inc., Maple Grove, Minn.

[21] Appl. No.: 692,299

[22] Filed: Aug. 5, 1996

Related U.S. Application Data

[63] Continuation of Ser. No. 404,948, Mar. 15, 1995, abandoned, which is a continuation of Ser. No. 227,185, Apr. 13, 1994, abandoned, which is a continuation of Ser. No. 862,994, Apr. 6, 1992, abandoned.

[51] Int. Cl.[6] .................................................. A61M 25/00
[52] U.S. Cl. ........................................ 604/96; 606/194
[58] Field of Search .......................... 604/96, 264, 280, 604/282; 606/191, 192, 194

[56] References Cited

U.S. PATENT DOCUMENTS

| | | |
|---|---|---|
| 883,583 | 3/1908 | Stallsmith . |
| 2,481,488 | 9/1949 | Auzin ........................... 18/58.7 |
| 3,087,493 | 4/1963 | Schossow ....................... 128/351 |
| 3,528,869 | 9/1970 | Derenuik ........................ 156/294 |
| 3,618,614 | 11/1971 | Flynn ............................ 128/348 |
| 3,634,924 | 1/1972 | Blake et al. .................... 29/447 |
| 3,865,666 | 2/1975 | Shoney ........................... 156/245 |
| 3,985,601 | 10/1976 | Panagrossi ...................... 156/229 |
| 4,072,146 | 2/1978 | Howes ........................... 128/2.05 D |
| 4,177,815 | 12/1979 | Patel ............................ 128/349 B |
| 4,195,637 | 4/1980 | Gruntzig et al. ................ 128/348 |
| 4,207,900 | 6/1980 | Patel et al. .................... 128/349 B |
| 4,210,478 | 7/1980 | Shoney ........................... 156/242 |
| 4,251,305 | 2/1981 | Becker et al. ................... 156/86 |
| 4,342,316 | 8/1982 | Rosenberg ....................... 128/349 B |
| 4,405,313 | 9/1983 | Sisley et al. ................... 604/43 |
| 4,406,653 | 9/1983 | Nunez ........................... 604/103 |
| 4,498,473 | 2/1985 | Gereg ........................... 128/207.15 |
| 4,597,755 | 7/1986 | Samson et al. ................... 604/96 |
| 4,661,095 | 4/1987 | Taller et al. ................... 604/103 |
| 4,739,768 | 4/1988 | Engelson ........................ 128/658 |
| 4,751,924 | 6/1988 | Hammerschmidt et al. ........... 128/207.15 |
| 4,762,129 | 8/1988 | Bonzel ........................... 128/344 |
| 4,771,777 | 9/1988 | Horzewski et al. ................ 128/344 |
| 4,775,371 | 10/1988 | Mueller, Jr. .................... 604/280 |
| 4,782,834 | 11/1988 | Maguire et al. .................. 128/344 |
| 4,790,315 | 12/1988 | Mueller, Jr. et al. ............. 128/344 |
| 4,820,349 | 4/1989 | Saab ............................ 604/96 X |
| 4,850,969 | 7/1989 | Jackson ......................... 604/96 |
| 4,863,442 | 9/1989 | DeMello et al. .................. 604/282 |
| 4,877,031 | 10/1989 | Conway et al. ................... 128/344 |
| 4,892,519 | 1/1990 | Songer et al. ................... 604/96 |
| 4,906,241 | 3/1990 | Noddin et al. ................... 606/194 |
| 4,913,701 | 4/1990 | Tower ........................... 604/103 |
| 4,943,278 | 7/1990 | Euteneuer et al. ................ 604/96 |
| 4,944,745 | 7/1990 | Sogard et al. ................... 606/194 |

(List continued on next page.)

FOREIGN PATENT DOCUMENTS

0347458A1  1/1988  European Pat. Off. .

OTHER PUBLICATIONS

Sales literature from Advanced Cardiovascular Systems, Inc., "Harzler Micro XT Dilation Catheter", published on or before Apr. 6, 1992.

Sales literature from Advanced Cardiovascular Systems, Inc., "Simpson Ultra–Low Profile II with Microglide Coating", published on or before Apr. 6, 1992.

Webster's II New Riverside University Dictionary, The Riverside Publishing Company, p. 275 1984.

*Primary Examiner*—Corrine M. McDermott
*Attorney, Agent, or Firm*—Nawrocki, Rooney & Sivertson, P.A.

[57] ABSTRACT

A dilation catheter having a shaft divided into a proximal portion and a distal portion. A dilation balloon is attached to the distal portion of the shaft. The proximal portion of the catheter may have a coating or a sleeve applied thereto to stiffen the proximal portion of the shaft. Alternatively, a dual lumen tube forms the proximal portion of the shaft while two separate tubes form the distal portion of the shaft thus making the distal portion more flexible then the proximal portion of the shaft.

10 Claims, 3 Drawing Sheets

U.S. PATENT DOCUMENTS

| | | | |
|---|---|---|---|
| 4,958,634 | 9/1990 | Jang | 606/194 |
| 4,963,313 | 10/1990 | Noddin et al. | 264/573 |
| 4,976,690 | 12/1990 | Solar et al. | 604/96 |
| 4,981,478 | 1/1991 | Evard et al. | 604/282 |
| 4,994,032 | 2/1991 | Sugiyama et al. | 604/96 |
| 4,998,917 | 3/1991 | Gaiser et al. | 604/96 |
| 5,002,559 | 3/1991 | Tower | 606/194 |
| 5,015,230 | 5/1991 | Martin et al. | 604/96 |
| 5,040,548 | 8/1991 | Yock | 128/898 |
| 5,085,649 | 2/1992 | Flynn | 604/282 |
| 5,087,247 | 2/1992 | Horn et al. | 604/98 |
| 5,209,729 | 5/1993 | Hofmann et al. | 604/96 |
| 5,217,440 | 6/1993 | Frassica | 604/282 |
| 5,261,879 | 11/1993 | Brill | 604/96 |
| 5,306,247 | 4/1994 | Pfenninger | 604/96 |
| 5,364,347 | 11/1994 | Jang | 604/53 |
| 5,370,615 | 12/1994 | Johnson | 604/96 |
| 5,496,275 | 3/1996 | Sirhan et al. | 604/96 |

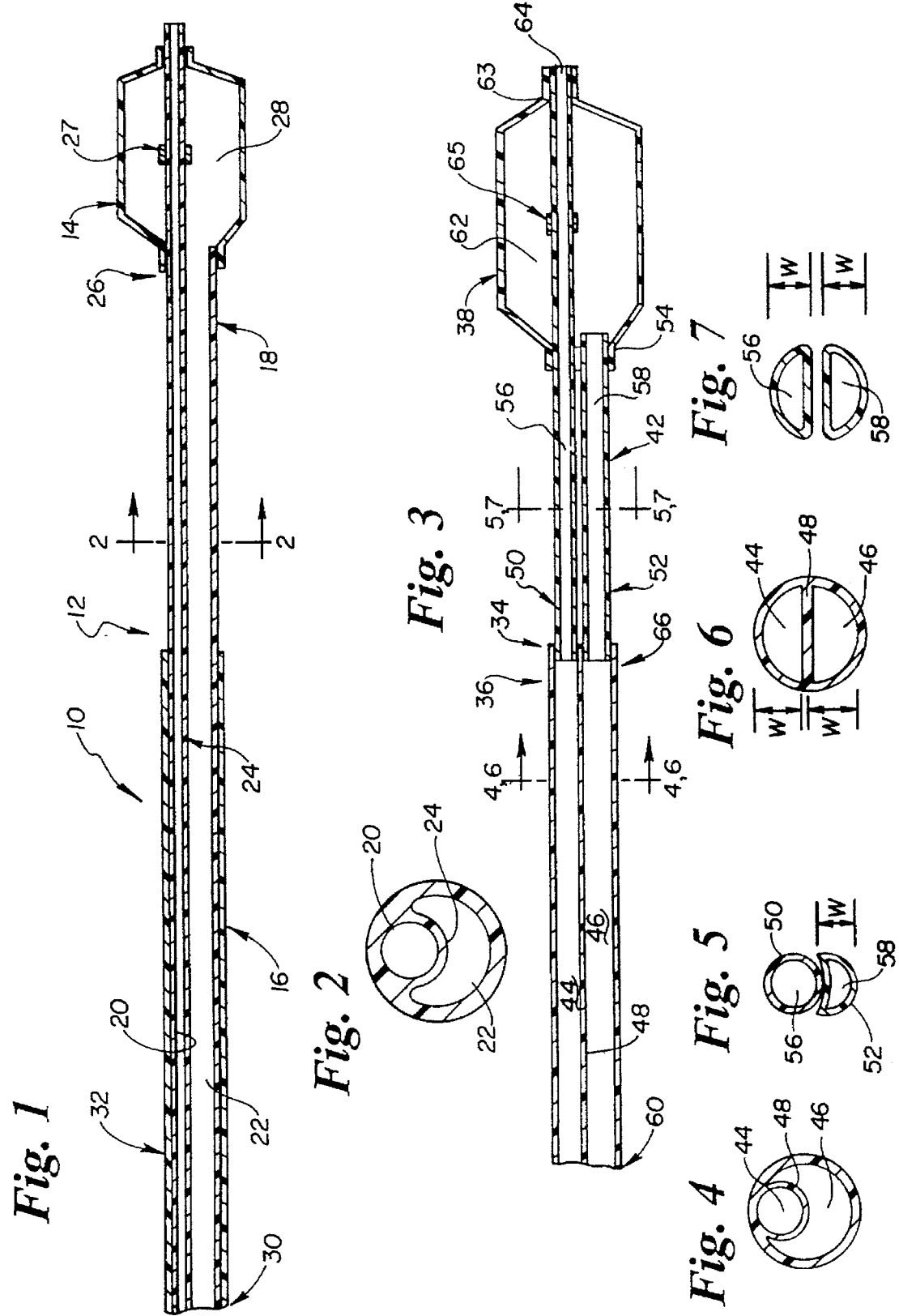

VARIABLE STIFFNESS MULTI-LUMEN CATHETER

This application is a continuation of U.S. patent application Ser. No. 08/404,948, filed Mar. 15, 1995, entitled "VARIABLE STIFFNESS MULTI-LUMEN CATHETER-" now abandoned, which is a continuation of U.S. patent application Ser. No. 08/227,185, filed Apr. 13, 1994, entitled "VARIABLE STIFFNESS MULTI-LUMEN CATHETER", now abandoned, which is a continuation of U.S. patent application Ser. No. 07/862,994, filed Apr. 6, 1992, entitled "VARIABLE STIFFNESS MULTI-LUMEN CATHETER", now abandoned.

BACKGROUND OF THE INVENTION

1. Field of the Invention

The present invention is directed to the field of angioplasty and, in particular, to a multi-lumen dilation catheter having variable stiffness along the length of the catheter to provide sufficient pushability while maintaining distal flexibility.

2. Description of the Prior Art

Angioplasty has gained wide acceptance in recent years as an efficient and effective method for treating certain types of vascular diseases. In particular, angioplasty is widely used for expanding a constricted area or lesion in a coronary artery. It is also used for treatment of lesions in other parts of the vascular system as well.

The most widely used form of angioplasty makes use of a balloon dilation catheter which is introduced into a patient's vascular system and is positioned across a stenosis. The balloon is inflated by supplying fluid under pressure through an inflation lumen connected to the balloon. The inflation of the balloon imparts a stretching force to the stenosis or artery wall to reestablish an acceptable blood flow through the artery.

There are various types of catheters available and one category of catheter is referred to as an over the wire (OTW) catheter. An OTW catheter is used in conjunction with a separate guide wire to cross a narrowed site in a person's vascular system. In this type of procedure, the guide wire is first advanced through the vasculature to or near the site of the lesion. After the guide wire is properly positioned, the catheter is advanced or guided over the guide wire so that the balloon portion is at the narrowed site.

OTW angioplasty balloon catheters generally have one of two types of construction, a coaxial construction or a multi-lumen construction. The coaxial construction has an inner tube which defines an inner lumen and an outer tube coaxially disposed about the inner tube to define an outer lumen between the walls of the tubes. The inner lumen typically will have a guide wire running therethrough while the outer lumen conveys inflation fluid from the proximal end of the catheter to the inflatable balloon. The multi-lumen design has a catheter shaft formed from a singular tubular extrusion with two or more lumens extending longitudinally and side-by-side through the shaft. One lumen is occupied by a guide wire and the other lumen(s) is (are) used to convey an inflation fluid from the proximal end of the catheter to the inflatable balloon.

Each design provides certain advantages. One advantage of the coaxial design, for example, is that the proximal portion of the outer tube can be formed from a relatively stiff material to provide increased "pushability" to the catheter. Another advantage is that the outer and inner tubes can be necked down in the distal region of the catheter and under the proximal waist of the balloon to reduce the distal shaft diameter and the profile of the catheter in its deflated state. A further advantage is that the coaxial design is symmetrically flexible in all directions. In addition, the coaxial catheter allows some degree of relative movement to take place between the inner tube and the outer tube when the catheter is bent which also increases the flexibility.

One advantage of the dual lumen design is its simple construction. First, only a single tube is extruded even though the number of lumens therein may vary. Secondly, there are fewer pieces associated with a dual lumen catheter thereby reducing the cost of fabrication and the complexity of assembly.

Dual lumen designs, however, have some disadvantages typically not associated with coaxial catheters. As discussed above, generally, dual lumen catheters have uniform flexibility over the entire shaft length and are often less flexible than coaxial catheters over the distal shaft because they are formed from a single extrusion tube. There have been efforts, however, to increase the flexibility of dual lumen catheters.

For example, Maguire et al., U.S. Pat. No. 4,782,834, discloses a dual lumen dilation catheter having a plurality of sections of different stiffness to provide optimum strength and flexibility at different points along the length of the catheter. The plurality of sections of the catheter are joined together by heat melting to form a unitary structure.

Conway et al., U.S. Pat. No. 4,877,031, discloses a dilation catheter which perfuses blood distally of the dilation balloon during inflation thereof. The lumen used for the distal perfusion of blood is separate from the lumen receiving the guide wire. The catheter may have a tubular structure formed from a material such as polyimide with an outer coating of resin impregnated fibrous material which has been wound or braided into the tubular substructure to provide a relatively stiff proximal portion and a relatively flexible but diametrically rigid distal portion.

SUMMARY OF THE INVENTION

The dilation catheter of the present invention includes a shaft with a first and a second longitudinally extending lumen positioned side-by-side. The shaft has a proximal portion and a distal portion, the distal portion having greater flexibility than the proximal portion. An inflatable balloon is mounted on the distal portion of the shaft with the second longitudinally extending lumen in fluid communication with the interior of the inflatable balloon. The flexibility of the proximal portion of the shaft may be reduced by applying a stiffening coating or sleeve onto the proximal portion. Alternately, the flexibility of the distal portion of the shaft may be increased by utilizing separate tubes for the first and second lumens in the distal portion of the shaft.

It is an object of the present invention to provide a dual lumen catheter having variable stiffness along the length of the catheter to provide the pushability needed to advance the catheter to the obstruction site in the vascular system while maintaining the flexibility of the catheter at its distal end.

It is another object of the present invention to reduce the proximal balloon profile of the dual lumen catheter by necking the shaft at the proximal waist of the balloon.

Further objects and advantages of this invention will become more apparent and readily appreciated from the following detailed description of the present invention with reference to the accompanying drawings.

BRIEF DESCRIPTION OF THE DRAWINGS

FIG. 1 is a cross-sectional view of a first preferred embodiment of a dual lumen catheter according to the present invention.

FIG. 2 is a cross-sectional view of the shaft of the catheter shown in FIG. 1.

FIG. 3 is a cross-sectional view of a second preferred embodiment of a dual lumen catheter according to the present invention.

FIG. 4 is a cross-sectional view of the proximal portion of the shaft of the catheter shown in FIG. 3.

FIG. 5 is a cross-sectional view of the distal portion of the shaft of the catheter shown in FIG. 3.

FIG. 6 is a cross-sectional view of the proximal portion of the shaft of the catheter shown in FIG. 3 according to a third preferred embodiment of the present invention.

FIG. 7 is a cross-sectional view of the distal portion of the shaft of the catheter shown in FIG. 3 according to a third preferred embodiment of the present invention.

DETAILED DESCRIPTION OF THE PRESENTLY PREFERRED EMBODIMENTS

Figure 8:
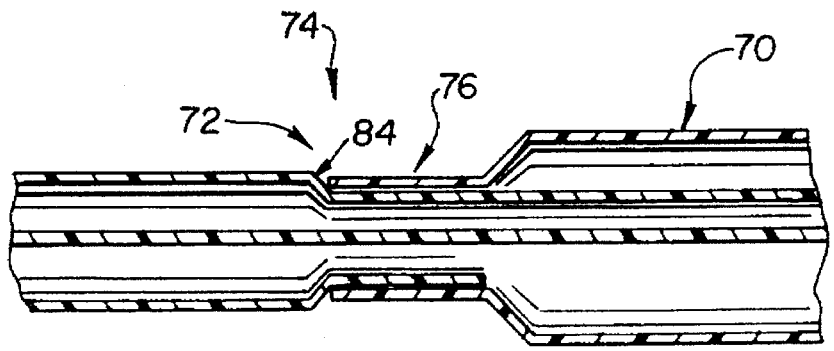
FIG. 8 is a cross-sectional view of the proximal waist portion of a balloon attached to the distal portion of a dual lumen catheter according to a fourth embodiment of the present invention.

FIG. 1 is a cross-sectional view of a dual lumen dilation catheter 10 according to a first preferred embodiment of the present invention. According to the first preferred embodiment of the present invention, the column strength of the proximal portion of the shaft may be increased by applying a stiffening coating or sleeve onto the proximal portion.

As illustrated in FIG. 1, the dilation catheter 10 has a shaft 12 and an inflatable balloon 14. The shaft 12 has a proximal portion 16 and a distal portion 18. The balloon 14 is attached to the shaft 12 at the distal portion 18. Extending longitudinally through the shaft 12 is a first lumen 20 and a second lumen 22. The first and second lumens 20 and 22 are positioned side-by-side and are separated by a common wall 24. The first lumen 20 extends through the balloon 14 while the second lumen 22 has been stripped away at the proximal end 26 of the balloon 14 so that the second lumen 22 can communicate with the interior 28 of the balloon 14. Although not illustrated, the catheter 10 has a manifold attached to the proximal end 30 of the proximal portion 16 of the shaft 12. The proximal portion 16 of the shaft 12 and the manifold are secured together by suitable adhesive bonding means such as urethane adhesive 3549 from the 3M Corporation of St. Paul, Minn. Dual lumen manifolds are well known in the art and need not be further described.

FIG. 2 illustrates a cross-section of the shaft 12 of the catheter 10 shown in FIG. 1. The first lumen 20 is illustrated as circular, however, it is not necessary that the lumen be circularly shaped as will be shown with reference to FIGS. 6 and 7. The dual lumen catheter 10 according to the present invention is intended to be used with standard sized guide wires. The guide wire lumen 20 therefore must be properly sized to allow the guide wire to comfortably pass therethrough. Preferably a guide wire for use with this embodiment will have a diameter of 0.014" or less so that the guide wire lumen will have an inner diameter preferably of 0.017" to 0.018". Guide wires having a diameter of 0.018" are also common and the guide wire lumen could be designed to accommodate a guide wire of that size. The second or inflation lumen 22 is shown to have generally a C-shape although it may have other configurations as will be described for example with reference to FIGS. 5–7.

The shaft 12 is preferably composed of a high or medium density polyethylene(PE) and most preferably a medium density polyethylene which gives the shaft 12 sufficient flexibility. A suitable balloon material is polyolefin which has been treated by radiation crosslinking. A suitable polyolefin is available from E. I. DuPont Nemours & Co. located at Wilmington, Del. under the trade name SURLYN® Ionomer as Resin No. 8527. Other suitable materials include a polyethylene terephthalate or a ethhylene vinyl acetate. The balloon 14 may be silicone coated to reduce frictional resistance. A urethane adhesive such as Urethane 3507 available from the H. B. Fuller Company of St. Paul, Minn., may be used to bond the balloon 14 to the distal portion of the shaft 12.

As shown in FIG. 1, the proximal portion 16 of the shaft 12 has a coating 32 applied thereto. The coating 32 is preferably formed of a polymeric material such as polytetraflouroethylene, nylon, polyimide, polyester or most preferably polyurethane. The coating 32 is applied to the proximal portion 16 of the shaft 12 to stiffen the shaft 12 so that the catheter 10 has better pushability while maintaining flexibility in the distal portion 18 of the shaft 12. In an exemplary embodiment, the proximal portion 16 of the shaft 12 before the coating is applied has an outer diameter preferably ranging from 0.039" to 0.042" with a wall thickness preferably ranging from 0.0030" to 0.0035." The coating thickness preferably ranges from 0.001" to 0.002" when either nylon, polyimide, polytetraflouroethylene, polyester or polyurethane is used as the coating material.

There are a number of methods to apply the stiffening coating or sheath to the proximal shaft. A coating may be applied to the shaft by dipping or spray coating the proximal portion 16 of the shaft 12, in the coating material which has been dissolved in a solvent. A polyurethane such as Estane 5715 from BF Goodrich Co. of Cleveland, Ohio may be dissolved in tetrahydrofuran from Aldrich Chemical Co. of Milwaukee, Wis. at approximately 10% concentration by weight to apply the stiffening material through spray or dip coating. Alternatively the coating 32 material may be applied by first forming a tube of the material and then shrinking or bonding that tube over the proximal shaft 12. It may also be possible to co-extrude the coating 32 along with the proximal portion 16 of the shaft 12.

In a preferred embodiment, the coating 32 is tapered in thickness in the transition region leading from the proximal portion 16 to the distal portion 18 of the shaft 12. An abrupt termination of the coating can cause greater stress at the transition region when the catheter is bent and can cause kinking of the shaft. Tapering the coating provides a gradual flexibility transition which is advantageous when the flexibilities of the proximal and distal portions of the shaft are very different.

The two preferred methods which can be used to taper the coating 32 in the transition region. The first is to apply the coating in multiple layers with the number of layers in the transition region decreasing in the distal direction of the shaft. The second method varies the thickness of the layers of the coating. The thickness of the layer of coating is dependent upon the concentration of the coating solution and the speed at which the tubing is drawn out of the solution. The thickness of a layer can be varied by varying the speed at which the tubing is drawn out of the solution. Increasing the draw speed will result in a thicker coating.

The shaft 12 is provided with a lubricous coating to reduce frictional resistance. The outer surface of the entire shaft 12 is coated with silicone. The inner surface of the guide wire lumen 20 may also be coated with silicone to reduce friction between the lumen wall and a guide wire.

At least one band marker 27 is provided about the guide wire lumen 20 (preferably centered within the interior 28 of balloon 14) to aid in determining the position of the catheter 10 via fluoroscopy during the angioplasty procedure.

Preferably, some of the plastic parts of the catheter are plasma treated to increase their bonding characteristics. For example, the shaft and manifold (not shown) may be plasma treated using helium or oxygen plasma treating techniques.

The present invention has the advantage of providing a dual lumen catheter having increased stiffness along the proximal length of the catheter to provide the pushability or column strength needed to advance the catheter to the obstruction site while maintaining the flexibility of the catheter at its distal end.

FIG. 3 is a cross-sectional view of a dual lumen dilation catheter 34 according to a second preferred embodiment of the present invention. According to the second preferred embodiment of the present invention, the flexibility of the distal portion of the shaft may be increased by utilizing separate tubes for the first and second lumens in the distal portion of the shaft.

As illustrated in FIG. 3, the dual lumen dilation catheter 34 has a shaft 36 and an inflatable balloon 38. The shaft 36 has a proximal portion 40 and a distal portion 42. The balloon 38 is attached to the shaft 36 at the distal portion 42. Extending longitudinally through the proximal portion 40 of the shaft 36 is a first lumen 44 and a second lumen 46. The first and second lumens 44 and 46 are positioned side-by-side and separated by a common wall 48.

Extending longitudinally through the distal portion 42 of the shaft 36 is a first tube 50 and a second tube 52. The first and second tubes 50 and 52 are parallel to one another and may be connected at various points along the distal portion 42 of the shaft 36 by ultrasonic welding or bonding for example as is well known in the art. The first tube 50 has a lumen 56 therein which communicates with the first lumen 44 of the proximal portion 40 of the shaft 36. The second tube 52 has a lumen 58 therein which communicates with the second lumen 46 of the proximal portion 40 of the shaft 36. The first tube 50 extends through the entire length of the balloon 32 while the second tube 52 ends at the proximal end 54 of the balloon 38.

As discussed with reference to FIG. 1, the catheter 34 has a manifold (not shown) attached to the proximal end 60 of the proximal portion 40 of the shaft 36. The manifold and shaft 32 are secured together in the same manner as described with respect to FIG. 1. The second lumen 46 is connected to an inflation port in the manifold so that the second lumen 46 transports inflation fluid from the inflation port to the second tube 52 which transports the fluid to the interior 62 of the balloon 38.

As described with reference to FIG. 1, the first lumen 44 of the first tube 50 has a guide wire (not shown) disposed therein from the proximal end 60 of the catheter 34 to a distal end 64 thereof.

FIG. 4 illustrates a cross-section of the proximal portion 40 of the shaft 36 of the catheter 34 shown in FIG. 3. The first and second lumens 44 and 46 have the same shape and dimensions as those shown in FIG. 2 and therefore further description is not needed.

FIG. 5 illustrates a cross-section of the distal portion 42 of the shaft 36 of the catheter 34 shown in FIG. 3. Separate first and second tubes 50 and 52 each have lumens 56 and 58 respectively which communicate with the first and second lumens 44 and 46 in the proximal portion 40 of the shaft 36. The lumens 56 and 58 are not separated by a common wall as in the proximal portion 40 of the shaft 36. The first tube 50 has generally the same shape as the first lumen 44 and preferably has an inner diameter of about 0.017" and an outer diameter of about 0.023". The second tube 52 can have generally the same shape as the second lumen 46 or it can be wider and thinner like a ribbon. In either case the second tube 52 preferably has a width marked "w" ranging from 0.005" to 0.014" and a wall thickness ranging from 0.0025 to 0.0035".

The first and second tubes 50 and 52 in the distal portion 42 of the shaft 36 are positioned adjacent to and parallel with one another. The first and second tubes 50 and 52 may be connected at various points along the length of the distal portion 42 of the shaft 36. The tubes 50 and 52 may be connected by bands wrapped around the outer surface of the tubes. The bands must be very flexible and thin walled such as a polymeric shrink sleeve, for example. Preferably the tubes 50 and 52 are connected by ultraviolet (uv) spot welding the joining surfaces of the tubes as is well known in the art. Alternatively, the second tube 52 can be coiled around the first tube 50 along the length of the distal portion 42 of the shaft 36. Coiling the inflation tube 52 around the guide wire tube 50 creates an uneven, bumpy outer surface of the shaft 36 in the distal portion 42. In order to reduce the degree of unevenness of the outer surface of the shaft 36, the inflation tube 52 is given a thin and wide shape with rounded outer surface like a ribbon as described above, as opposed to a more circular configuration. The unevenness will be reduced and thus the surface of the distal portion 42 of the shaft 36 will be smoother.

FIG. 6 illustrates a cross-section of the proximal portion 40 of the shaft 36 of the catheter 34 shown in FIG. 3 according to a third embodiment of the present invention. The first lumen 44 and the second lumen 46 are both symmetrical and D-shaped instead of the circular and C-shaped lumens shown in FIG. 4. Preferably the first lumen 44 has a width marked "w" of about 0.017– and the second lumen 46 has a width marked "w" of about 0.014".

FIG. 7 illustrates a cross-section of the distal portion 42 of the shaft 36 of the catheter 34 shown in FIG. 3 according to the third embodiment of the present invention. The first and second tubes 50 and 52 are both symmetrical and D-shaped. As described with reference to FIGS. 4 and 5, the first and second lumens 44 and 46 in the proximal portion 40 of the shaft 36 communicate with the lumens 56 and 58 in the distal portion 42 of the shaft 36. The first and second tubes 50 and 52 can be connected at interval points (not shown) along the length of the distal portion 42 of the shaft 36 as described above. Preferably the width marked "w" of the guide wire lumen is about 0.017" and the width marked "w" of the inflation lumen is about 0.014". The thickness of the walls of the guide wire tube 50 and inflation tube 52 preferably ranges from 0.0030" to 0.0035". The outer diameter of the distal portion 42 of the shaft 36 is preferably about 0.040."

The proximal portion 40 of the shaft 36 may be formed of polyethylene (PE), preferably medium or high density PE and most preferably a high density PE. The proximal shaft 40 may be formed by extrusion as is well known in the art.

The first guide wire tube 50 in the distal portion 42 of the shaft 36 may also be formed of polyethylene, preferably medium or high density and most preferably high density while the second inflation tube 52 is preferably formed of a medium density polyethylene. The distal portion 42 of the shaft preferably ranges from 5 to 15 inches in length.

The shaft 34 is provided with a lubricous coating (such as silicone) to reduce frictional resistance. A suitable coating thickness is about 0.0005 in. A suitable balloon material is a polyolefin which has been treated by radiation cross linking. A suitable polyolefin is available from E. I. DuPont Nemours & Co. located at Wilmington, Del. under the trade name SURLYN® Ionomer as Resin No. 8527. Other suitable materials include polyethylene terephthalate or ethylene vinyl acetate as discussed above. The balloon 38 may also be silicone coated to reduce frictional resistance.

Preferably the proximal waist 54 of the balloon 38 is joined to the first and second tubes 50 and 52 and the distal waist 63 of the balloon 38 is joined to the distal end 64 of the first tube 50 by a heat seal. Generally, there are two methods to create a heat seal and both are well known to those skilled in the art. The first method is to shrink the proximal waist 54 and the distal waist 63 of the balloon 38 around the shaft 36. This method is preferred if the balloon material and the shaft material are not compatible. The second method is to weld the proximal and distal waists 54 and 63 of the balloon 38 onto the shaft 36. This method is preferred if the balloon material and the shaft material are compatible. The heat source for either shrinking or welding the balloon to the catheter shaft preferably utilizes RF or resistive heating.

Alternatively, an adhesive may be used to bond the proximal waist 54 of the balloon 38 to the first and second tubes 50 and 52 and the distal waist 63 of the balloon 38 to the distal end 64 of the first tube 50. Since flexibility is critical in the distal portion 42 of the catheter 34, the adhesive is preferably a high viscosity urethane. In addition, there may be voids between the proximal and distal waists 54 and 63 of the balloon 38 and the distal portion 42 of the shaft 36 to which the balloon 38 is bonded. A high viscosity urethane helps to fill those voids and reduce the possibility of leakage.

The distal portion 42 of the shaft 36 may be formed preferably by extruding separate tubes 50 and 52 and bonding the separate tubes 50 and 52 to the distal end 66 of the proximal portion of the shaft 36. Preferably the first and second tubes 50 and 52 are bonded to the distal end 66 of the proximal portion 40 of the shaft 36 by a heat seal as described above.

Alternatively, the first and second tubes 50 and 52 may be bonded to the distal end 66 of the proximal portion 40 of the shaft 36 by an adhesive, preferably a urethane adhesive.

Alternatively, one lumen of a dual lumen tubing can be stripped away in the distal portion of the tubing. The removed lumen is replaced by a separate tube to form the inflation tube. The separate tube is bonded to the dual lumen tubing as described above so as to continue the removed lumen in the distal portion of the tubing.

The catheter 34 shown in FIGS. 3–7 provides a multi-lumen proximal shaft portion 40 and two separate tubes 50 and 52 in the distal portion 42 of the shaft 36. The proximal portion 42 is stiffer than the distal portion 40 of the shaft because of the multi-lumen tubing and the tubing material differences. This stiffness and column strength is a benefit to the performance of the catheter 34. Flexibility is nevertheless maintained in the distal portion 42 of the shaft 36 by using separate tubes to continue the guide wire and inflation lumens at the distal end 66 of the proximal portion 40 of the shaft 36 to the balloon 38.

At least one band marker 65 is provided about the guide wire lumen 44 (preferably centered within the interior of the balloon 62) to aid in determining the position of the catheter 34 via fluoroscopy during the angioplasty procedure.

Preferably, some of the plastic parts of the catheter are plasma treated to increase their bonding characteristics. For example, the shaft and manifold (not shown) may be plasma treated using helium or oxygen plasma treating techniques.

FIG. 8 is a cross-sectional view of the distal portion 74 of a dual lumen dilation catheter according to a fourth embodiment of the present invention. As an alternative to bonding the balloon of the catheter to the shaft by means of a heat seal as described above, an adhesive can be used.

In order to reduce the profile of the balloon 70 in its deflated state, the diameter of the shaft 72 at the distal portion 74 is reduced from the diameter of the shaft 72 at the proximal portion (not shown) by necking the distal portion 74 of the shaft 72. Those skilled in the art will be familiar with the process of necking. Generally, a tapered die is used which is heated to approximately the glass transition temperature of the tubing or slightly above and the end of the tube is inserted into the die and pulled through the die. Necking of the tubing is thus accomplished by a combination of a temperature at or above the glass transition temperature of the tubing material and a minimal applied tensile force. In order to neck a dual lumen tubing such as the one shown in FIG. 1, a mandrel is placed in the guide wire lumen 20 to prevent the lumen from closing during the necking process. Generally, the guide wire lumen 20 will remain the same size while the inflation lumen 22 is reduced, however, the guide wire lumen 20 may be slightly redirected. With reference to the catheter illustrated in FIG. 3, the profile of the distal portion 42 of the shaft 36 may be reduced by necking the inflation tube 52.

The proximal waist 76 of the balloon 70 is bonded to the necked portion 84 of the shaft 72 by an adhesive bond. The necked distal portion 84 of the shaft 72 allows the catheter to have a smaller profile over the proximal portion of the balloon when the balloon 70 is in a deflated state.

Figure 9:
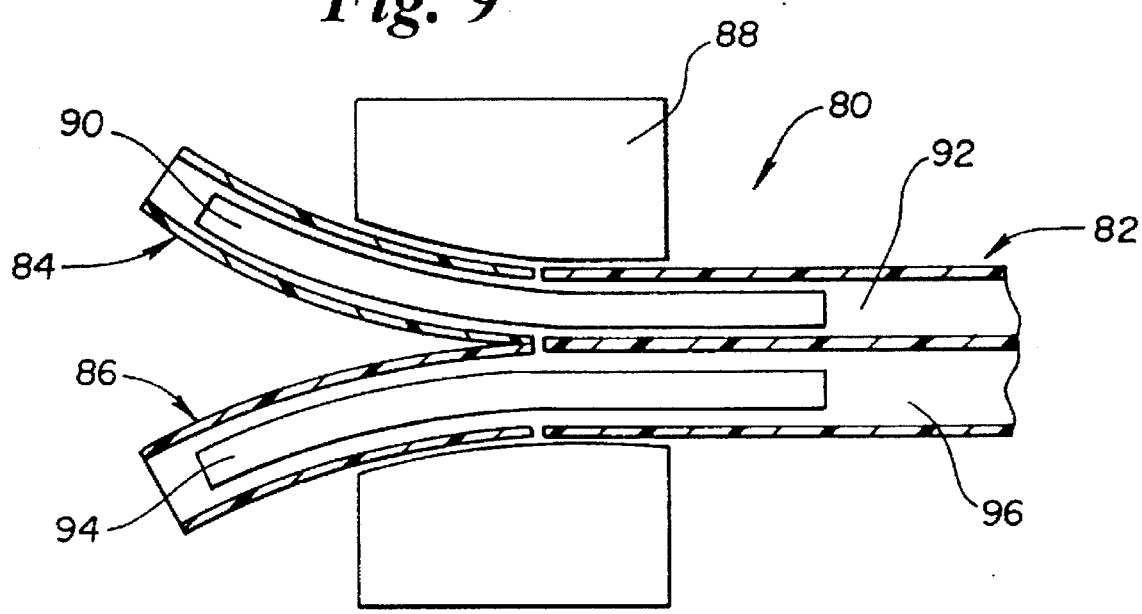
FIG. 9 illustrates a method of forming the proximal end of a dual lumen catheter according to the present invention.
Figure 10:
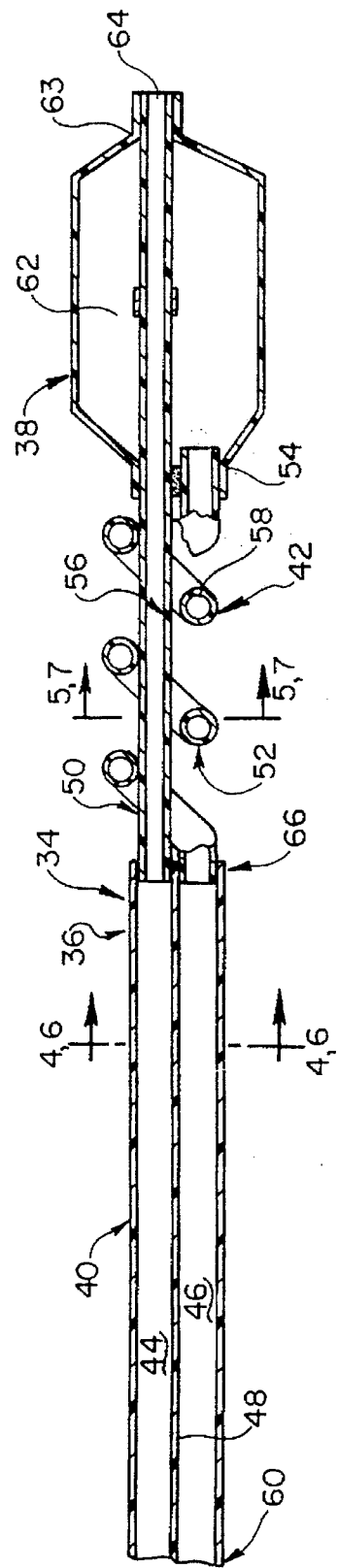
FIG. 10 is a cross-sectional view of a fifth preferred embodiment of a dual lumen catheter according to the present invention.
Figure 11:
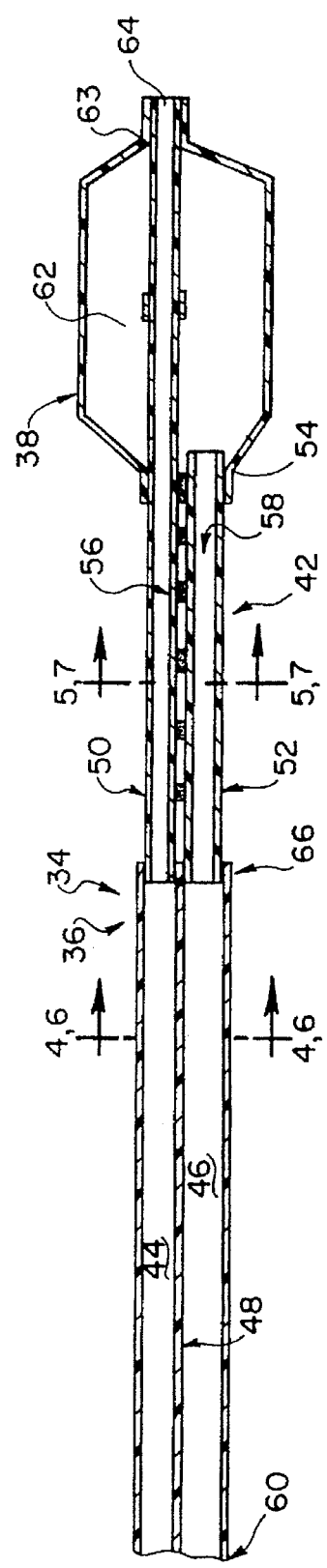
FIG. 11 is a cross-section view of a sixth preferred embodiment of a dual lumen catheter according to the present invention.

FIG. 9 illustrates a method of forming the proximal end 80 of a dual lumen catheter according to the present invention. The dual lumen tubing 82 must separate at the proximal end 80 of the catheter into two isolated tubes 84 and 86 so that one tube can be attached to an inflation device, for example, while the other tube is attached to an introducer. A mold 88 is used to create the desired proximal portion 80 of the catheter. The mold 88 defines a tapered hole with some type of heating element built in such as a resistance or radio frequency heating element, for example.

A first mandrel 90 is placed in the single lumen tube 84 and is advanced so that the mandrel 90 extends into a first lumen 92 in the dual lumen tubing. A second mandrel 94 is placed in the single lumen tube 86 and is advanced so that the mandrel 94 extends into the second lumen 96 in the dual lumen tubing. The mandrels 90 and 94 keep the lumens open in tubes 82, 84, and 86. The region where the tubes 82, 84, and 86 meet is placed in the mold 88. The mold 88 is heated and the tubes 84 and 86 are melted or welded onto the end of the dual lumen tube 82. The mandrels 90 and 94 maintain the integrity of the lumens so that the lumen in the first tube 84 communicates with lumen 92 of the dual lumen tube 82 while the lumen in the second tube 86 communicates with the other lumen 96 of the dual lumen tube 82. A protective housing is then molded or bonded over this joint region and molded luer fittings are attached to the ends of the two separate tubes. The manifold facilitates the connection of inflation devices, introducers, and other equipment to the dual lumen catheter.

While a dual lumen dilation catheter has been specifically illustrated, the present invention is not limited to a dual lumen catheter but rather equally applies to multiple lumen catheters.

While the invention has been shown and described in connection with particular preferred embodiments, it is apparent that certain changes and modifications, in addition to those mentioned above, may be made by those who are skilled in the art without departing from the basic features of the present invention. Accordingly, it is the intention of the Applicant to protect all variations and modifications within the true spirit and valid scope of the invention.

What is claimed is:

1. An apparatus comprising:
   a. a dilatation catheter shaft including a first tubular member having a longitudinal axis with a proximal end and a distal end adapted to receive a removable guide wire and including a second tubular member having a longitudinal axis with a proximal end and a distal end, wherein said second tubular member extends adjacent and exterior to said first tubular member over a portion of the length thereof, wherein said longitudinal axis of said first tubular member extends generally parallel to said longitudinal axis of said second tubular member; and
   b. a dilatation balloon in fluid communication with said distal end of said second tubular member wherein said dilatation catheter shaft is relatively more flexible at said distal end than said proximal end.

2. An over-the-wire dilatation catheter comprising:
   a shaft including a length of a single tubular member formed by a single extrusion, the shaft having a distal portion and a proximal portion and having an inflation lumen and a guide wire lumen, said inflation lumen and said guide wire lumen separated by a common wall;
   a dilatation balloon connected to the distal portion of said shaft wherein said guide wire lumen extends through the dilatation balloon and said inflation lumen communicates with the interior of the dilatation balloon; and
   the shaft having varying flexibility along at least a portion of its length proximal of the balloon wherein the varying flexibility is provided by a coating applied to the proximal portion of the tubular member and wherein the thickness of said coating decreases gradually from the proximal end to the distal end of the coating segment of the tubular member so as to create a gradual transition in the flexibility of the tubular member.

3. An over-the-wire dilatation catheter comprising:
   a shaft having a proximal portion and a distal portion, said proximal portion having a first and a second lumen, said first and second lumens separated by a common wall, said distal portion having a third and a fourth lumen, said third and fourth lumens defined by a first tubular member, having a longitudinal axis, and a second tubular member having a longitudinal axis, respectively; said first tubular member being separate from said second tubular member and co-extending exterior of said second tubular member, wherein said longitudinal axis of said first tubular member extends generally parallel to said longitudinal axis of said second tubular member; and
   a dilatation balloon connected to the distal portion of the shaft wherein the third lumen continues the first lumen through the interior of the dilatation balloon and the fourth lumen connects the interior of the dilatation balloon with the second lumen.

4. A catheter according to claim 3 wherein said first tubular member and said second tubular member are joined together at various points along the distal portion of the catheter.

5. A catheter according to claim 3 wherein said proximal portion of said shaft is constructed from a different material than either of said first and second tubular members in said distal portion of said shaft.

6. The over-the-wire dilatation catheter of claim 3, wherein said longitudinal axis of said first tubular member is laterally displaced from said longitudinal axis of said second tubular member.

7. An over-the-wire catheter comprising:
   a shaft having a proximal portion, a distal portion, an inflation lumen and a guide wire lumen, said inflation lumen and said guide wire lumen separated by a common wall in at least the proximal portion of the shaft; said distal portion of the shaft being formed by a first tubular member having a longitudinal axis and a first lumen therethrough and a second tubular member having a longitudinal axis and a second lumen therethrough, said first tubular member extending coextensively along the exterior of said second tubular member, wherein said longitudinal axis of said first tubular member extends generally parallel to said longitudinal axis of said second tubular member, said first lumen continuing said guide wire lumen through said balloon and said second lumen continuing said inflation lumen; and
   a balloon connected to the distal portion of said shaft wherein said second lumen communicates with the interior of the balloon.

8. A catheter according to claim 7 wherein said first tubular member is formed of a different material than said second tubular member.

9. A catheter according to claim 7 wherein said first and second tubular members are joined together at various points along the distal portion of the catheter.

10. The over-the-wire dilatation catheter of claim 7, wherein said longitudinal axis of said first tubular member is laterally displaced from said longitudinal axis of said second tubular member.

* * * * *